Figure 1:
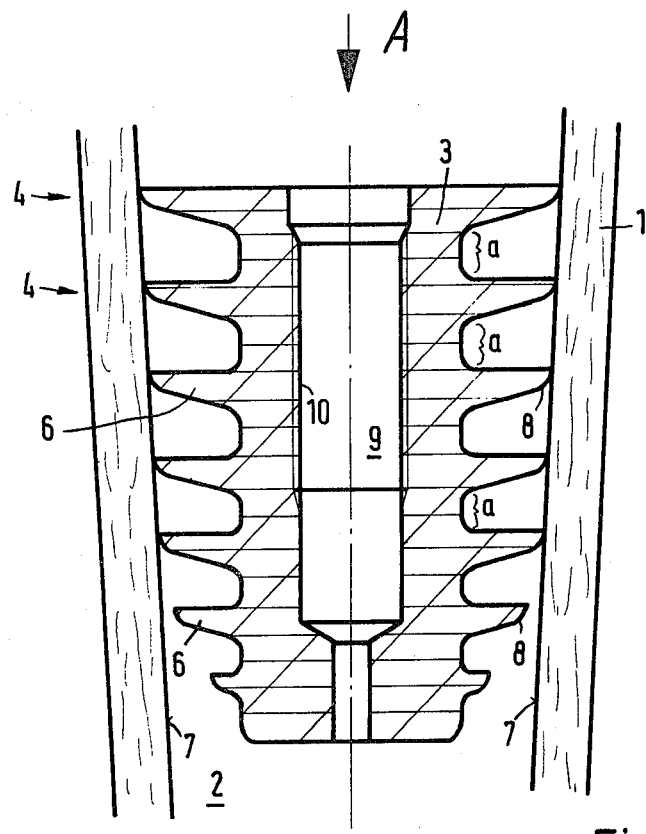

United States Patent [19]

Stuhmer

[11] 4,245,359
[45] Jan. 20, 1981

[54] PLUG FOR OPENINGS PRODUCED BY OPERATIVE PROCEDURES IN MEDULLATED BONES

[75] Inventor: Karl-Gerhard Stuhmer, Ravensburg, Fed. Rep. of Germany

[73] Assignee: Sulzer Brothers Limited, Winterthur, Switzerland

[21] Appl. No.: 21,182

[22] Filed: Mar. 16, 1979

[30] Foreign Application Priority Data

Mar. 28, 1978 [CH] Switzerland .................. 3282/78

[51] Int. Cl.³ .................. A61F 1/00; A61F 1/24
[52] U.S. Cl. .................. 3/1.9; 3/1.91; 128/92 C
[58] Field of Search .................. 3/1.9–1.913, 3/1; 128/92 C, 92 CA

[56] References Cited

U.S. PATENT DOCUMENTS

| | | | |
|---|---|---|---|
| 3,866,321 | 2/1975 | Valen | 128/92 C UX |
| 3,905,109 | 9/1975 | Cohen | 32/10 A X |
| 4,167,047 | 9/1979 | Grundei et al. | 3/1.91 |

FOREIGN PATENT DOCUMENTS

| | | | |
|---|---|---|---|
| 1046920 | 7/1953 | France | 128/92 C |
| 1443470 | 7/1976 | United Kingdom | 3/1.9 |

OTHER PUBLICATIONS

"Silastic Intramedullary Implant (Swanson Design) Brand", Pamphlet by Dow Corning Corp., Medical Products Division, Midland, Mich., Jan. 1969, pp. 1–9.

*Primary Examiner*—Ronald L. Frinks
*Attorney, Agent, or Firm*—Kenyon & Kenyon

[57] ABSTRACT

The plug is made of a plastics material and acts as a cement barrier for openings produced by an operative procedure in medullated bones. The plug is clamped between the side walls of the opening of the bone by means of elastic flanges and prevents the bone cement from escaping downwards on insertion of a intramedullary stem.

11 Claims, 2 Drawing Figures

PLUG FOR OPENINGS PRODUCED BY OPERATIVE PROCEDURES IN MEDULLATED BONES

This invention relates to a plug for insertion in an opening formed in a medullated bone. More particularly, this invention relates to a plug for insertion in a medullated bone in which an intramedullary stem of an endoprosthesis is to be anchored by means of bone cement.

As is known, when an endoprosthesis is to be anchored in a bone by means of a bone cement, the cement is first introduced into an operatively prepared opening in the bone and then when the cement has turned to a pasty consistency, a stem of the prosthesis is pressed or knocked into the pasty substance. However, a difficulty may arise during this process because the bone cement which is present in the opening and which should be displaced as far as possible against the side walls of the opening and along the stem axis, is, instead, pressed further into the bone in the axial direction of the stem or opening.

Accordingly, it is an object of the invention to prevent an axial displacement of a bone cement in a bone opening during insertion of an intramedullary stem of an endoprosthesis.

It is another object of the invention to permit an effective anchoring of an endoprosthesis stem within a bone.

Briefly, the invention provides a plug which can be inserted into an opening operatively formed in a medullated bone in order to prevent axial displacement of a subsequently inserted bone cement when a stem of an endoprosthesis is inserted in the opening. The plug is formed with a plurality of coaxial rings which are disposed in axially spaced relation along a longitudinal axis of the plug. Each ring is also formed with a plurality of circumferentially spaced radially directed flanges which define alternating slots of radially outwardly increasing width. Each flange is also elastically deformable at least axially of the plug.

When used, the plug which preferably consists of a plastics conventional in implant technique, for example, high molecular polyethylene (HDPE), is inserted into an opening which has been made in a bone such that the elastically deformable flanges of the plug are bent upwards towards the mouth of the opening in the style of a calyx consisting of a number of layers and are clamped in the side walls of the opening. In this way, the flanges serve to extensively shut off the opening in the axial direction. The flanges can be adapted to the operative opening in the bone, for example, by keeping different sizes in stock. Thereupon, a bone cement of known type is introduced into the operation cavity.

The use of a plurality of axially successive rings increases the adhesion of the plug in the side walls of a bone. Thus, after a setting procedure, the plug can only be moved insignificantly in the axial direction even with the stem being pressed into the cement. Insertion of the plug into the bone opening can be facilitated and pushing out in the opposite direction can be prevented if the free ends of the flanges are rounded on the side facing into the opening and have sharp edges on the other side, i.e., the side facing the mouth of the opening.

The plug can be centered in the bone opening if the radial length of the flanges of the individual rings increases axially at least over part of the axial height of the plug. Further, the calyx formation can be facilitated if the axial distance between the individual rings also increases in the direction of increasing radial lengths of the flanges.

Pressure equalization on the two sides of the plug can be obtained by means of a centrally disposed passage in the plug. Further, means may be provided within the passage for releaseably receiving a setting instrument. For example, the means may be in the form of a screw thread into which the setting instrument can be threaded. The passage can also be used for extracting blood and bone splinters from the part of the opening situated beyond the plug as considered from the operation aperture.

Figure 2:
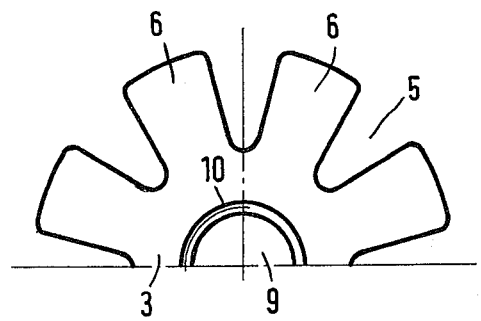

These and other objects and advantages of the invention will become more apparent from the following detailed description and appended claims taken in conjunction with the accompanying drawings in which:

FIG. 1 illustrates a diagrammatic longitudinal sectional view through a plug according to the invention after insertion in an opening in a bone; and FIG. 2 illustrates a view taken in the direction of arrow A in FIG. 1.

Referring to FIG. 1, the bone 1 is provided with a downwardly tapering opening 2, as viewed, which is produced by a known operative procedure so as to receive an intramedullary stem of an endoprosthesis (not shown) with the spongy tissue of the bone having been at least extensively removed. A plug 3 which acts as a cement barrier is pushed into the downwardly tapering opening 2. As shown, the plug 3 has a cylindrical shank from which a plurality of rings 4 of circumferentially spaced apart radial flanges 6 extend. As shown in FIG. 2, the flanges 6 of each ring 4 define alternating slots 5 of radially outwardly increasing width.

The rings 4 are distributed over the axial length of the plug 3 while the flanges 6 of the respective rings are either offset from one another circumferentially or arranged in alignment axially of the plug 3.

The plug 3 is preferably made from a plastics which is suitable for implanting in a bone. In addition, the flanges 6 of the plug are elastically deformable at least axially of the plug 3 so that when the plug 3 is pressed into the bone opening 2, the flanges 6 are bent upwardly, as viewed, in the style of a calyx. In so doing, the flanges 6 clamp against the inner walls 7 of the bone 1 and thus insure that the plug 3 fits tightly in the opening 2.

FIG. 1 illustrates an intermediate stage in the insertion of the plug 3 between loose and tight. In this stage, the elastic flanges 6 just touch the wall 7 of the bone opening 2 and are not yet bent up in the form of a calyx and clamped. As shown in FIG. 1, the radially elastic lengths of the flanges 6 increase in the upward direction, as viewed, and, for this reason, the distances a between the individual rings 4 also increase in the same direction so that sufficient room is available for the longer flanges 6 as they bend upwardly.

The flanges 6 of the plug define a conically shaped envelope of increasing dimension in the upward direction, as viewed, and thus facilitates centering of the plug 3 upon insertion into the bone opening 2.

Each flange 6 as a free end with a rounded side 8, (the bottom, as viewed) and a sharp edge on the opposite side (the top side, as viewed). The sharp edges inhibit the serrated plug 3 from being pushed out of the bone opening 2 and improve the clamping of the flanges 6 against the walls 7.

As shown in FIG. 1, the plug 3 has a centrally disposed axial passage 9 which has a portion of reduced cross-sectional shape at the lower end, as viewed. In addition, the passage 9 may have a means such as a screw thread 10 for releaseably receiving a setting instrument (not shown), for example, a rod shaped to correspond to the axial configuration of the opening and which may have depth markers for the depth to which the plug 3 has been inserted as measured from the edge of the operation aperture for the opening 2. The rod may also have a screw thread cooperating with the screw thread 10 at one end and a handle at the other end.

When the plug 3 is in place within the bone 1, a cement suitable for anchoring a stem of an endoprosthesis is placed within the opening of the bone 1 above the plug 3. The stem (not shown) of the endoprosthesis may then be pushed or tapped into the cement in the usual fashion. Because of the presence of the plug 3, the cement is inhibited from moving axially into the opening 2 but rather tends to flow radially outwardly along the side walls 7 of the opening above the stem. Some cement may flow into the passage 9 of the plug 3; however, because the passage 9 is counterbored with a reduced cross-section, the amount of the cement which passes through is reduced to a minimum.

What is claimed is:

1. A plug for insertion in an opening formed in a medullated bone to act as a cement barrier, said plug having a plurality of coaxial rings disposed in axially spaced relation along a longitudinal axis of said plug, each said ring including a plurality of circumferentially spaced radially directed flanges defining alternating slots of radially outwardly increasing width, each said flange being elastically deformable at least axially of said plug.

2. A plug as set forth in claim 1 wherein said flanges are of increasing radial length axially at least over part of the axial length of said plug.

3. A plug as set forth in claim 2 wherein said rings are spaced apart axially on an increasing spacing in the direction of increasing radial length.

4. A plug as set forth in claim 1 having a centrally disposed axial passage therethrough.

5. A plug as set forth in claim 4 having means in said passage for releaseably receiving a setting instrument therein.

6. A plug as set forth in claim 1 wherein each flange has a free end with a rounded side and a sharp edge on an opposite side.

7. A plug as set forth in claim 1 made of plastics.

8. A plug as set forth in claim 7 having an axial passage extending therethrough, said passage having a portion of reduced cross-sectional shape at one end.

9. A plug as set forth in claim 8 wherein said flanges define a conically-shaped envelope of increasing dimension in a direction away from said one end.

10. A plug as set forth in claim 9 wherein said flanges are of increasing radial length in a direction away from said one end.

11. A plug for insertion in an opening formed in a medullated bone to act as a cement barrier, said plug having a plurality of coaxial rings disposed in axially spaced relation along a longitudinal axis of said plug, each said ring including a plurality of circumferentially spaced radially directed flanges defining alternating slots of radially outwardly increasing width, said flanges being elastically deformable at least axially of said plug to be bent towards the mouth of the opening in the bone in the style of a calyx to shut off the opening in an axial direction.

* * * * *